(12) United States Patent
Siskin et al.

(10) Patent No.: US 8,152,903 B2
(45) Date of Patent: Apr. 10, 2012

(54) HINDERED CYCLIC POLYAMINES AND THEIR SALTS FOR ACID GAS SCRUBBING PROCESS

(75) Inventors: Michael Siskin, Westfield, NJ (US); Alan R Katritzky, Gainesville, FL (US); Edmund J. Mozeleski, Califon, NJ (US); Frank Cheng-Yu Wang, Annandale, NJ (US)

(73) Assignee: ExxonMobile Research & Engineering Company, Annandale, NJ (US)

( * ) Notice: Subject to any disclaimer, the term of this patent is extended or adjusted under 35 U.S.C. 154(b) by 375 days.

(21) Appl. No.: 11/989,152

(22) PCT Filed: Jul. 21, 2006

(86) PCT No.: PCT/US2006/028688
§ 371 (c)(1),
(2), (4) Date: Aug. 13, 2009

(87) PCT Pub. No.: WO2007/021464
PCT Pub. Date: Feb. 22, 2007

(65) Prior Publication Data
US 2009/0297414 A1     Dec. 3, 2009

(51) Int. Cl.
*B01D 53/14*     (2006.01)
(52) U.S. Cl. .......... 95/236; 423/228; 544/347; 564/506; 564/505; 564/508; 564/1; 564/503; 95/235
(58) Field of Classification Search .................. 423/228, 423/223, 226, 232, 234; 544/347; 564/506, 564/503, 505, 508
See application file for complete search history.

(56) References Cited

U.S. PATENT DOCUMENTS

| | | | |
|---|---|---|---|
| 4,112,051 A | 9/1978 | Sartori et al. | |
| 4,112,052 A | 9/1978 | Sartori et al. | |
| 4,183,903 A * | 1/1980 | Melchior et al. | 423/226 |
| 4,217,238 A | 8/1980 | Sartori et al. | |
| 4,240,922 A | 12/1980 | Sartori et al. | |
| 4,376,101 A * | 3/1983 | Sartori et al. | 423/223 |
| 4,376,102 A | 3/1983 | Thaler et al. | |
| 4,405,578 A | 9/1983 | Sartori et al. | |
| 4,405,580 A | 9/1983 | Stogryn et al. | |
| 4,405,581 A | 9/1983 | Savage et al. | |
| 4,405,585 A | 9/1983 | Sartori et al. | |
| 4,405,811 A * | 9/1983 | Stogryn et al. | 564/506 |
| 4,483,833 A | 11/1984 | Stogryn et al. | |
| 4,525,294 A | 6/1985 | Sartori et al. | |
| 4,581,209 A | 4/1986 | Oswald et al. | |
| 4,618,481 A | 10/1986 | Heinzelmann et al. | |
| 4,759,866 A | 7/1988 | Shulik et al. | |
| 4,892,674 A | 1/1990 | Ho et al. | |
| 4,897,091 A * | 1/1990 | Pasternak et al. | 95/46 |
| 5,167,941 A * | 12/1992 | Bedell | 423/242.2 |
| 5,209,914 A * | 5/1993 | Peytavy et al. | 423/228 |
| 5,413,627 A * | 5/1995 | Landeck et al. | 95/235 |
| 5,602,279 A * | 2/1997 | Thaler et al. | 562/526 |
| 5,629,322 A * | 5/1997 | Guthikonda et al. | 514/313 |
| 7,938,887 B2 * | 5/2011 | Rochelle et al. | 95/159 |

FOREIGN PATENT DOCUMENTS
GB        2017524        10/1979

* cited by examiner

*Primary Examiner* — Duane Smith
*Assistant Examiner* — Ives Wu
(74) *Attorney, Agent, or Firm* — Malcolm D. Keen; Glenn T. Barrett

(57) ABSTRACT

Hindered cyclic polyamines and their salts are absorbents useful in acid gas treatment processes.

16 Claims, 1 Drawing Sheet

Adsorption-Regeneration Unit for Selective H₂S Removal

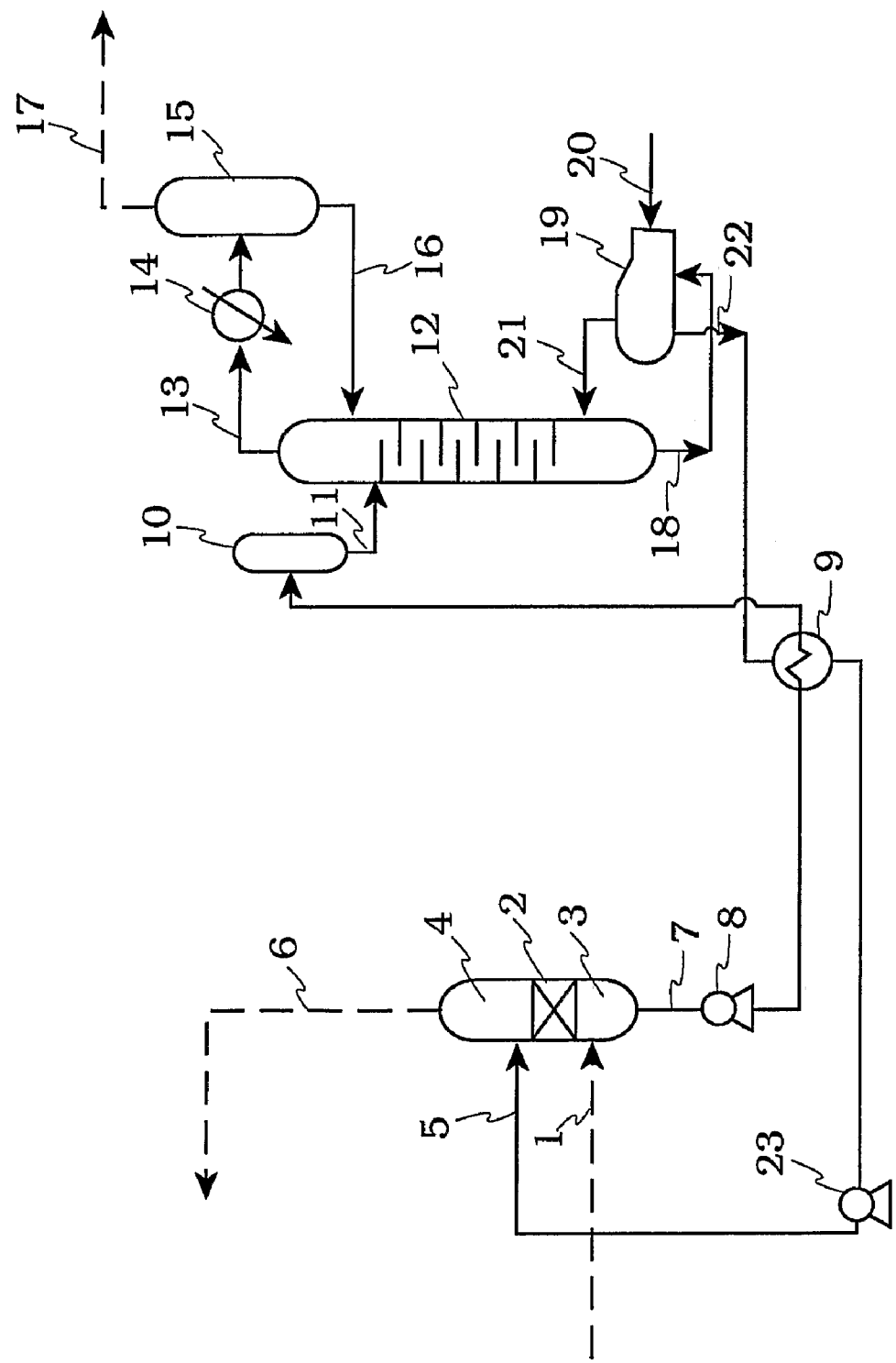

US 8,152,903 B2

HINDERED CYCLIC POLYAMINES AND THEIR SALTS FOR ACID GAS SCRUBBING PROCESS

BACKGROUND OF THE INVENTION

1. Field of the Invention

The present invention relates to an absorbent composition and to a process for the selective absorption of $H_2S$ from an $H_2S$-containing gas using the absorbent composition.

2. Description of the Related Art

It is well known in the art to treat gases and liquids, such as mixtures containing acidic gases including $CO_2$, $H_2S$, $CS_2$, HCN, COS and oxygen and sulfur derivatives of $C_1$ to $C_4$ hydrocarbons with amine solutions to remove these acidic gases. The amine usually contacts the acidic gases and the liquids as an aqueous solution containing the amine in an absorber tower with the aqueous amine solution contacting the acidic fluid countercurrently.

The treatment of acid gas mixtures containing, inter alia, $CO_2$ and $H_2S$ with amine solutions typically results in the simultaneous removal of substantial amounts of both the $CO_2$ and $H_2S$. For example, in one such process generally referred to as the "aqueous amine process", relatively concentrated amine solutions are employed. A recent improvement of this process involves the use of sterically hindered amines as described in U.S. Pat. No. 4,112,052, to obtain nearly complete removal of acid gases such as $CO_2$ and $H_2S$. This type of process may be used where the partial pressures of the $CO_2$ and related gases are low. Another process often used for specialized applications where the partial pressure of $CO_2$ is extremely high and/or where many acid gases are present, e.g., $H_2S$, COS, $CH_3SH$ and $CS_2$ involves the use of an amine in combination with a physical absorbent, generally referred to as the "nonaqueous solvent process". An improvement on this process involves the use of sterically hindered amines and organic solvents as the physical absorbent such as described in U.S. Pat. No. 4,112,051.

It is often desirable, however, to treat acid gas mixtures containing both $CO_2$ and $H_2S$ so as to remove the $H_2S$ selectively from the mixture, thereby minimizing removal of the $CO_2$. Selective removal of $H_2S$ results in a relatively high $H_2S/CO_2$ ratio in the separated acid gas which simplifies the conversion of $H_2S$ to elemental sulfur using the Claus process.

The typical reactions of aqueous secondary and tertiary amines with $CO_2$ and $H_2S$ can be represented as follows:

$$H_2S + R_3N \rightleftharpoons R_3NH^+ + SH^- \quad (1)$$

$$H_2S + R_2NH \rightleftharpoons R_2NH_2^+ + SH^- \quad (2)$$

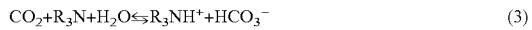

$$CO_2 + R_3N + H_2O \rightleftharpoons R_3NH^+ + HCO_3^- \quad (3)$$

$$CO_2 + 2R_2NH \rightleftharpoons R_2NH_2^+ + R_2NCOO^- \quad (4)$$

$$RNH_2 + CO_2 \rightleftharpoons RN^+H_2CO_2^- \quad (5)$$

$$RN^+H_2CO_2 + RNH_2 \rightleftharpoons RNHCO_2^- RNH_3^+ \quad (6)$$

wherein each R is an organic radical which may be the same or different and may be substituted with a hydroxy group. The above reactions are reversible, and the partial pressures of both $CO_2$ and $H_2S$ are thus important in determining the degree to which the above reactions occur.

While selective $H_2S$ removal is applicable to a number of gas treating operations including treatment of hydrocarbon gases from shale pyrolysis, refinery gas and natural gas having a low $H_2S/CO_2$ ratio, it is particularly desirable in the treatment of gases wherein the partial pressure of $H_2S$ is relatively low compared to that of $CO_2$ because the capacity of an amine to absorb $H_2S$ from the latter type gases is very low. Examples of gases with relatively low partial pressures of $H_2S$ include synthetic gases made by coal gasification, sulfur plant tail gas and low-Joule fuel gases encountered in refineries where heavy residual oil is being thermally converted to lower molecular weight liquids and gases.

Although it is known that solutions of primary and secondary amines such as monoethanolamine (MEA), diethanolamine (DEA), dipropanolamine (DPA), and hydroxyethoxyethylamine (DGA) absorb both $H_2S$ and $CO_2$ gas, they have not proven especially satisfactory for preferential absorption of $H_2S$ to the exclusion of $CO_2$ because the amines undergo a facile reaction with $CO_2$ to form carbamates as shown in Equations 5 and 6.

Diisopropanolamine (DIPA) is relatively unique among secondary aminoalcohols in that it has been used industrially, alone or with a physical solvent such as sulfolane, for selective removal of $H_2S$ from gases containing $H_2S$ and $CO_2$, but contact times must be kept relatively short to take advantage of the faster reaction of $H_2S$ with the amine compared to the rate of $CO_2$ reaction shown in Equations 2 and 4 hereinabove.

In 1950, Frazier and Kohl, Ind. and Eng. Chem., 42, 2288 (1950) showed that the tertiary amine, methyldiethanolamine (MDEA), has a high degree of selectivity toward $H_2S$ absorption over $CO_2$. This greater selectivity was attributed to the relatively slow chemical reaction of $CO_2$ with tertiary amines as compared to the rapid chemical reaction of $H_2S$. The commercial usefulness of MDEA, however, is limited because of its restricted capacity for $H_2S$ loading and its limited ability to reduce the $H_2S$ content to the level at low pressures which is necessary for treating, for example, synthetic gases made by coal gasification.

Recently, U.K. Patent Publication No. 2,017,524 A to Shell disclosed that aqueous solutions of dialkylmonoalkanolamines, and particularly diethyl-monoethanolamine (DEAE), have higher selectivity and capacity for $H_2S$ removal at higher loading levels than MDEA solutions. Nevertheless, even DEAE is not very effective for the low $H_2S$ loading frequency encountered in the industry. Also, DEAE has a boiling point of 161° C., and as such, it is characterized as being a low-boiling, relatively highly volatile amino alcohol. Such high volatilities under most gas scrubbing conditions result in large material losses with consequent losses in economic advantages.

U.S. Pat. Nos. 4,405,581; 4,405,583 and 4,405,585 disclose the use of severely sterically hindered amine compounds for the selective removal of $H_2S$ in the presence of $CO_2$. Compared to aqueous methyldiethanolamine (MDEA) severely sterically hindered amines lead to much higher selectivity at high $H_2S$ loadings.

U.S. Pat. No. 4,112,052 is directed to a process for removing $CO_2$ from acid gases using an aqueous amine scrubbing solution. The amines used are sterically hindered amines containing at least one secondary amine group attached to either a secondary or tertiary carbon atom or a primary amino group attached to a tertiary carbon atom. The amines are selected to be at least partially soluble in the solvent used, i.e., water.

U.S. Pat. No. 4,376,102 discloses that acidic gases containing $CO_2$ are removed from normally gaseous mixtures by absorbing the $CO_2$ from the gaseous mixture using an aqueous solution comprising a basic alkali metal salt or hydroxide which contains (1) at least one diaminoalcohol of the formula

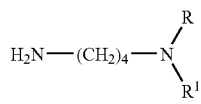

wherein R and R[1] are each independently a $C_1$-$C_6$ alkyl group and either R or R[1] or both R and R[1] have a pendent hydroxyl group and (2) an amino acid. The basic alkali metal salt or hydroxide are selected from the group consisting of alkali metal bicarbonates, carbonates, hydroxides, borates, phosphates and their mixtures. See also U.S. Pat. No. 4,376,101; U.S. Pat. No. 4,581,209; U.S. Pat. No. 4,217,238.

U.S. Pat. No. 4,525,294 is directed to amino acid mixtures, their alkali metal salts and processes for their preparation. The process involves the reductive condensation of glycine or alanine and their alkali metal salts with a ketone in the presence of a reluctant such as hydrogen and a catalytically effective amount of a hydrogenation catalyst. Thus, a reaction as follows is disclosed:

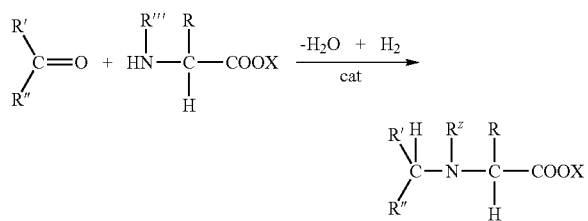

wherein R is hydrogen or methyl, X is hydrogen or an alkali metal such as sodium or potassium, R' and R" are selected from the group consisting of:
a) substituted or unsubstituted linear or branched alkayl radicals having one to 20 carbons; or
b) substituted or unsubstituted alkylene radicals each having three to six carbon atoms and combined to form a cyclic ring;
c) substituted or unsubstituted cycloalkyl radicals having from four to eight ring carbon atoms;
d) substituted or unsubstituted hydroxyl alkyl radicals, linear or branched, having one to 20 carbon atoms; or
e) substituted or unsubstituted arylalkyl radicals having from seven to 20 carbon atoms;
and $R^z$ is hydrogen or a substituted or unsubstituted linear alkyl radical having from 1 to 20 carbon atoms, or mixtures of hydrogen and such alkyl radicals.

U.S. Pat. No. 4,759,866 discloses primary sterically hindered amino acids of the formula:

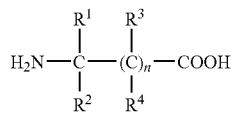

wherein R[1] and R[2] are independently selected from $CH_3$, $C_2H_5$ and $C_3H_7$, and R[3] and R[4] are independently hydrogen and $CH_3$ and n is zero, 2 or 3, for use as promoters for alkali metal salts in acid gas scrubbing.

U.S. Pat. No. 5,602,279 is directed to a gas treating composition prepared by reacting 2-amino-2-methyl-1-propanol with KOH, diluting with water and adding $K_2CO_3$ and a vanadium corrosion inhibitor. The acid gas scrubbing solution contains

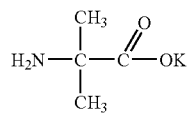

U.S. Pat. No. 4,618,481 is directed to an absorbent composition comprising a severely hindered amino compound and an amine salt for the absorption of $H_2S$ from gaseous mixtures. The severely sterically hindered amino compound can be a secondary amino ether alcohol, a disecondary amino ether, and mixtures thereof. The amine salt can be the reaction product of the aforesaid severely sterically hindered amino compound, a tertiary amino compound such as tertiary alkanolamines, triethanol amines, and mixtures thereof and a strong acid, or a thermally decomposable salt of a strong acid, i.e., ammonium salt or a component capable of forming a strong acid and mixtures thereof. Suitable strong acids include inorganic acids such as sulfuric acid, sulfurous acid, phosphoric acid, phosphorous acid, pyrophosphoric acid, an organic acid such as acetic acid, formic acid, adipic acid, benzoic acid, etc. Suitable salts of these acids include the ammonium slats, for example ammonium sulfate, ammonium sulfite, ammonium phosphate and mixtures thereof. Preferably ammonium sulfate (a salt) or $SO_2$ (a precursor of an acid) is used as reactant with the amine. Suitable amine salts are those that are non-volatile at conditions used to regenerate the absorbent composition.

U.S. Pat. No. 4,892,674 discloses to an absorbent composition comprising an alkaline absorbent solution containing a non-hindered amine and an additive of a severely-hindered amine salt and/or a severely-hindered aminoacid and to the use of the absorbent for the selective removal of $H_2S$ from gaseous streams. The amine salt is the reaction product of an alkaline severely hindered amino compound and a strong acid or a thermally decomposable salt of a strong acid, i.e., ammonium salt. Suitable strong acids include inorganic acids such as sulfuric acid, sulfurous acid, phosphoric acid, phosphorous acid, pyrophosphoric acid; organic acids such as acetic acid, formic acid, adipic acid, benzoic acid, etc. Suitable salts include the ammonium salts, for example, ammonium sulfate, ammonium sulfite, ammonium phosphate and mixtures thereof.

U.S. Pat. No. 4,240,922 discloses an amine-solvent liquid composition comprising (a) an amine mixture comprised of at least 50 mol % of a sterically hindered amine and at least about 10 mol % of a tertiary amine alcohol, wherein said sterically hindered amine contains at least one secondary amine group which is part of a ring and is attached to either a secondary or tertiary carbon atom or a primary amino group attached to a tertiary carbon atom, and (b) a non-reactive solvent for said amine mixture selected from sulfones, sulfoxides, glycols, mono and diethers thereof; 1,3 dioxo compounds characterized by being a 5- to 6-membered heterocyclic ring, aromatic ethers, aromatic hydrocarbons, pyrrolidines, piperidones and mixtures thereof.

U.S. Pat. No. 4,405,578 discloses an aqueous acid gas scrubbing composition comprising 10 to about 40 wt % of an alkali metal salt or hydroxide, about 2 to 20 wt % of a lower aliphatic monosubstituted amino acid and 2 to about 20 wt % of a sterically hindered diamine or triamine compound, said diamino compound being of the general formula

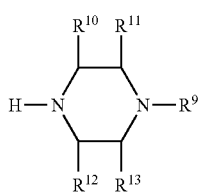

wherein $R^9$-$R^{13}$ are hydrogen, $C_1$-$C_3$ alkyl, $C_1$-$C_3$ amino alkyl, $C_1$-$C_3$ hydroxy-alkyl or $C_1$-$C_3$ carboxy alkyl radicals such that at least one of the groups $R^{10}$ and $R^{12}$ is different from hydrogen.

U.S. Pat. No. 4,405,580 discloses an absorbent solution of amino compounds defined as tertiary amino azabicyclic alcohols. These compounds have two fused rings which share at least one side, each have 4-10 ring atoms, preferably 4-7 ring atoms of which one ring atom is nitrogen. Each ring may be unsubstituted or substituted and the nitrogen atom forming the tertairy amino portion of the compound is saturated within the bicyclic framework at a bridgehead or new bridgehead ring position. The hydroxyl group if the alcohol may be directly connected to the ring or may be attached to a carbon chain arranged in a linear or branched fashion and connected to the heterocycle via a ring nitrogen or a ring carbon.

U.S. Pat. No. 4,483,833 discloses a scrubbing solution for the selective absorption of $H_2S$ from a normally gaseous mixture containing $H_2S$ and $CO_2$ comprising an amino compound having a pKa of at least about 8.6 and comprising a nitrogen heterocyclic tertiary amino alcohol or a nitrogen heterocyclic tertiary aminoether alkanol and a solvent which solubilizes the amino compound and is a physical absorbent. Among the compounds disclosed are:

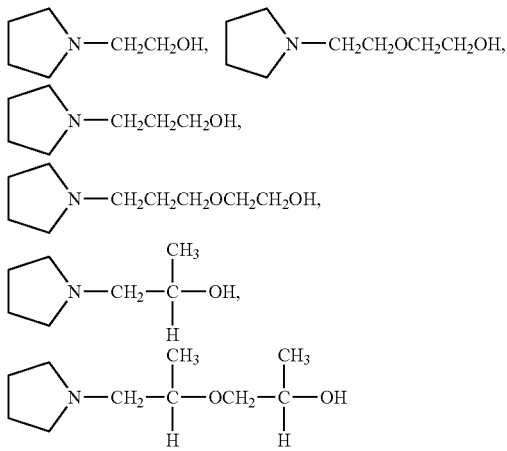

DESCRIPTION OF THE FIGURE

FIG. 1 is a diagrammatic flow sheet illustrating an absorption regeneration unit for the selective removal of $H_2S$ from gaseous streams containing $H_2S$ and $CO_2$.

SUMMARY OF THE INVENTION

Hindered cyclic poly amines are absorbents useful in acid gas treatment processes. The salts of such hindered cyclic poly amines are absorbents especially useful in acid gas treatment processes conducted in aqueous processing medium. Similarly oxygen functionalized hindered cyclic poly amines are absorbents useful in acid gas treatment processes conducted in aqueous processing medium.

DESCRIPTION OF THE INVENTION

The present invention is directed to hindered poly cyclic polyamine absorbents of the formula:

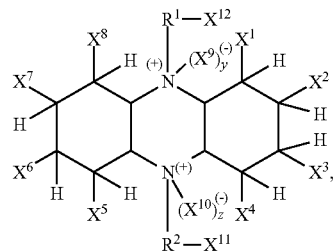

I

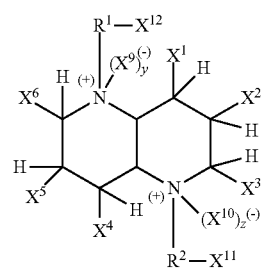

II and all isomers thereof, i.e.,

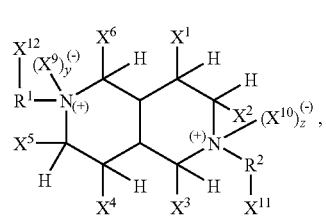

IIa

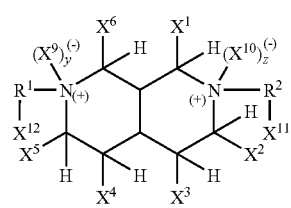

IIb

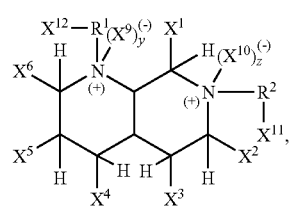

IIc

-continued

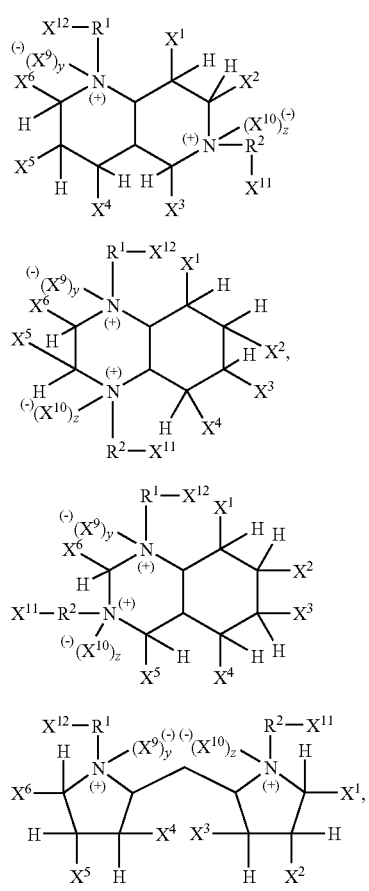

and all isomers thereof, i.e.,

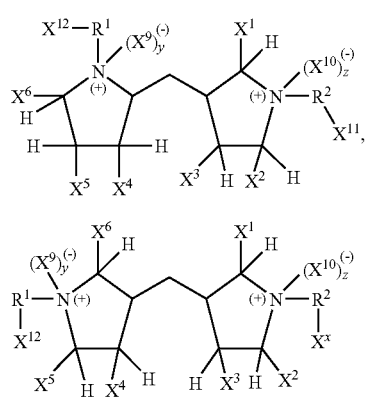

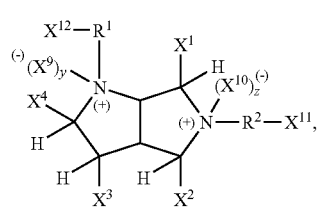

-continued

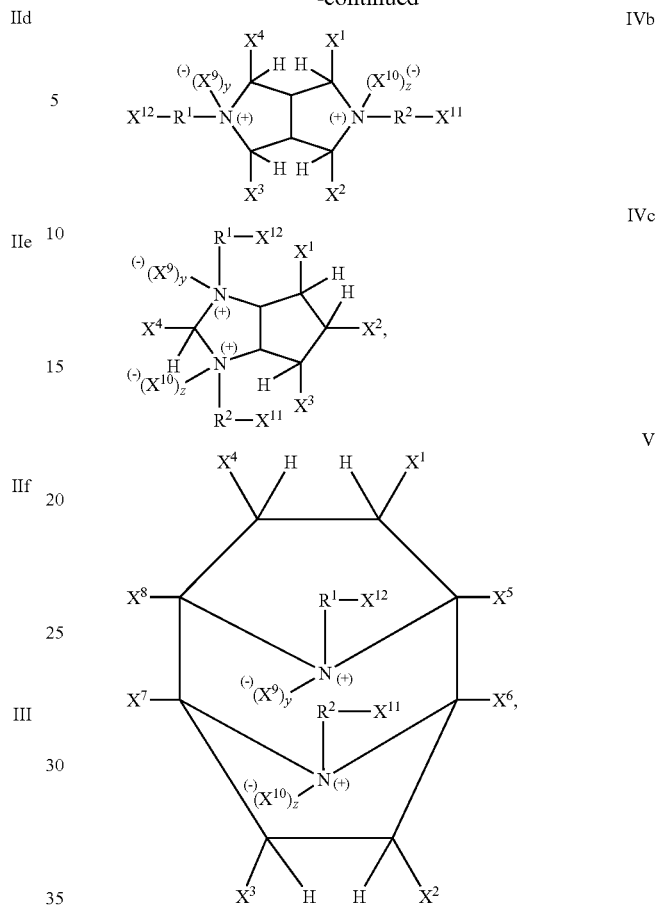

and all isomers thereof, i.e.,
wherein
$R^1$ and $R^2$ are the same or different and are selected from hydrogen methyl, ethyl, $C_3$-$C_9$ substituted or unsubstituted straight or branched alkyl, alkenyl, cycloalkyl, $C_6$-$C_9$ aryl, alkylaryl, arylalkyl;

$X^1$-$X^8$ are the same or different and are selected from hydrogen, methyl, ethyl, $C_3$-$C_9$ substituted or unsubstituted straight or branched alkyl, alkenyl, cycloalkyl, $C_6$-$C_9$ aryl, alkyl aryl, arylalkyl, a functional group containing one or more oxygens, preferably one or more of $X^1$-$X^8$ are a functional group containing one or more oxygen atoms, more preferably $X^1$-$X^8$ are selected from the group consisting of

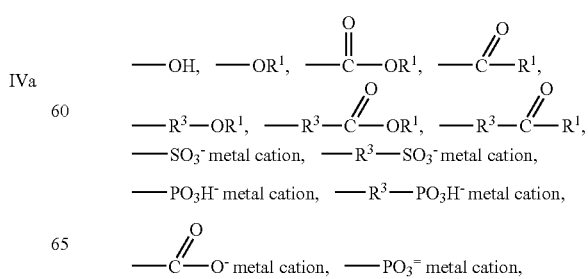

-continued

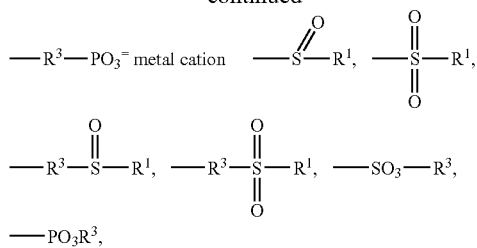

and mixtures thereof,
$X^9$ and $X^{10}$ are the same or different and are selected from $-^+(HO_3SR^4)$, $-^+(HO_3PR^4)$,

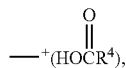

sulfonates, sulfates, sulfites, phosphates, phosphites, phosphonates, $C_1$-$C_9$ alkylates (e.g., acetates, formates), adipates, benzoates,
$X^{11}$ and $X^{12}$ are the same or different and are selected from hydrogen, a functional group containing one or more oxygens, preferably as defined for $X^1$-$X^8$, wherein when $R^1$ and/or $R^2$ are $C_2$ or greater the substituent $X^{11}$ or $X^{12}$,
when other than H, is on the #2 carbon or higher, that is, when $X^{11}$ or $X^{12}$ is other than H, $X^{11}$ or $X^{12}$ is not on the carbon directly attached to the nitrogen,
y is zero or 1,
z is zero or 1,
wherein at least one of y and z is 1 when $X^1$-$X^8$ and $X^{11}$ and $X^{12}$ are not functional groups containing at least one oxygen and wherein when one or more of $X^1$-$X^8$, $X^{11}$ and $X^{12}$ are functional groups containing at least one oxygen,
preferably both Y and Z are zero, in which case the nitrogen becomes a basic amine center,
provided that when any of $X^1$-$X^8$, $X^{11}$ or $X^{12}$ is a functional group containing a single oxygen (e.g., —OH, —$OR^1$,

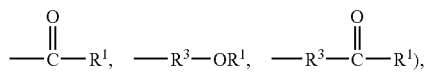

at least 2 of $X^1$ to $X^8$, $X^1$ or $X^{12}$ are such single oxygen containing functional group,
$R^3$ and $R^4$ are independently selected from $C_1$-$C_9$ alkyl, $C_2$-$C_9$ alkenyl, $C_3$-$C_9$ cycloalkyl, $C_6$-$C_9$ aryl, alkylaryl or arylalkyl, metal cation is one or more a monovalent, divalent or trivalent metal cation sufficient to satisfy the valence requirement of the anion or anion cluster, preferably Group I alkali metal (monovalent), Group II alkaline earth metal (divalent), aluminum, iron, most preferably Group I alkali metal or Group II alkaline earth metal. Salts formed from divalent cations can be half- or full-salts. Salts formed from trivalent cations can be one third-, two thirds- or full-salts. By anion cluster is meant 2 or more anions the valence requirement of which are satisfied by, e.g., a single divalent or trivalent metal cation.

The absorbents described above exhibit high selectivity for $H_2S$ and other acidic component removal from normally gaseous mixtures of said acidic components and gaseous non-acidic components, and $CO_2$ and retain their high selectivity and loading capacity even after regeneration.

One or more of the absorbents described are utilized for the selective absorption of acidic components, especially $H_2S$ from a normally gaseous mixture containing such acidic components, especially $H_2S$ and non-acidic components, and $CO_2$ comprising:

(a) contacting said normally gaseous mixture with an absorbent solution characterized as capable of selectively absorbing $H_2S$ from said mixture;

(b) regenerating, at least partially, said absorbent solution containing $H_2S$; and (c) recycling the regenerated solution for the selective absorption of $H_2S$ by contacting as in step (a).

Preferably, the regenerating step is carried out by heating and stripping and more preferably heating and stripping with steam.

The term "absorbent solution" as used herein includes but is not limited to solutions wherein the amino compound is dissolved in a solvent selected from water or a physical absorbent or mixtures thereof. Solvents which are physical absorbents (as opposed to the amino compounds which are chemical absorbents) are described, for example, in U.S. Pat. No. 4,112,051, the entire disclosure of which is incorporated herein by reference, and include, e.g., aliphatic acid amides, N-alkylated pyrrolidones, sulfones, sulfoxides, glycols and the mono- and diethers thereof. The preferred physical absorbents herein are sulfones, and most particularly, sulfolane. The preferred liquid medium comprises water.

The absorbent solution ordinarily has a concentration of amino compound of about 0.1 to 6 moles per liter of the total solution, and preferably 1 to 4 moles per liter, depending primarily on the specific amino compound employed and the solvent system utilized. If the solvent system is a mixture of water and a physical absorbent, the typical effective amount of the physical absorbent employed may vary from 0.1 to 5 moles per liter of total solution, and preferably from 0.5 to 3 moles per liter, depending mainly on the type of amino compound being utilized. The dependence of the concentration of amino compound on the particular compound employed is significant because increasing the concentration of amino compound may reduce the basicity of the absorbent solution, thereby adversely affecting its selectivity for $H_2S$ removal, particularly if the amino compound has a specific aqueous solubility limit which will determine maximum concentration levels within the range given above. It is important, therefore, that the proper concentration level appropriate for each particular amino compound be maintained to insure satisfactory results.

The solution of this invention may include a variety of additives typically employed in selective gas removal processes, e.g., antifoaming agents, antioxidants, corrosion inhibitors, and the like. The amount of these additives will typically be in the range that they are effective, i.e., an effective amount.

Also, the amino compounds described herein may be admixed with other amino compounds as a blend. The ratio of the respective amino compounds may vary widely, for example, from 1 to 99 wt % of the amino compounds described herein.

Three characteristics which are of ultimate importance in determining the effectiveness of the amino compounds herein for $H_2S$ removal are "selectivity", "loading" and "capacity". The term "selectivity" as used throughout the specification is defined as the following mole ratio fraction:

$$\frac{\text{(moles of } H_2S/\text{moles of } CO_2) \text{ in liquid phase}}{\text{(moles of } H_2S/\text{moles of } CO_2) \text{ in gaseous phase}}$$

The higher this fraction, the greater the selectivity of the absorbent solution for the $H_2S$ in the gas mixture.

By the term "loading" is meant the concentration of the $H_2S$ and $CO_2$ gases physically dissolved and chemically combined in the absorbent solution as expressed in moles of gas per moles of the amine. The best amino compounds are those which exhibit good selectivity up to a relatively high loading level. The amino compounds used in the practice of the present invention typically have a "selectivity" of not substantially less than 10 at a "loading" of 0.1 moles, preferably, a "selectivity" of not substantially less than 10 at a loading of 0.2 or more moles of $H_2S$ and $CO_2$ per moles of the amino compound.

"Capacity" is defined as the moles of $H_2S$ loaded in the absorbent solution at the end of the absorption step minus the moles of $H_2S$ loaded in the absorbent solution at the end of the desorption step. High capacity enables one to reduce the amount of amine solution to be circulated and use less heat or steam during regeneration.

The acid gas mixture herein necessarily includes $H_2S$, and may optionally include other gases such as $CO_2$, $N_2$, $CH_4$, $H_2$, CO, $H_2O$, COS, HCN, $C_2H_4$, $NH_3$, and the like. Often such gas mixtures are found in combustion gases, refinery gases, town gas, natural gas syn gas, water gas, propane, propylene, heavy hydrocarbon gases, etc. The absorbent solution herein is particularly effective when the gaseous mixture is a gas, obtained, for example, from a shale oil retort, coal liquefaction or gasification, liquefaction of heavy oil with steam, air/steam or oxygen/steam, thermal conversion of heavy residual oil to lower molecular weight liquids and gases, e.g., fluid coker, Flexicoker, delayed coker, or in sulfur plant tail gas cleanup operations.

The absorption step of this invention generally involves contacting the normally gaseous stream with the absorbent solution in any suitable contacting vessel. In such processes, the normally gaseous mixture containing $H_2S$ and $CO_2$ from which the $H_2S$ as well as other acidic components such as carbon disulfide, carbonyl sulfide and oxygen and sulfur derivatives of $C_1$-$C_4$ hydro-carbon can be selectively removed may be brought into intimate contact with the absorbent solution using conventional means, such as a tower or vessel packed with, for example, rings or with sieve plates, or a bubble reactor. Other acidic gaseous components will also be removed.

In a typical mode of practicing the invention, the absorption step is conducted by feeding the normally gaseous mixture into the lower portion of the absorption tower while fresh absorbent solution is fed into the upper region of the tower. The gaseous mixture, freed largely from the $H_2S$, emerges from the upper portion of the tower, and the loaded absorbent solution, which contains the selectively absorbed $H_2S$, leaves the tower near or at its bottom. Preferably, the inlet temperature of the absorbent solution during the absorption step is in the range of from about 20° C. to about 100° C., and more preferably from 30° C. to about 60° C. Pressures may vary widely; acceptable pressures are between 5 and 2000 psia, preferably 20 to 1500 psia, and most preferably 25 to 1000 psia in the absorber. The contacting takes place under conditions such that the $H_2S$ is selectively absorbed by the solution. The absorption conditions and apparatus are designed so as to minimize the residence time of the liquid in the absorber to reduce $CO_2$ pickup while at the same time maintaining sufficient residence time of gas mixture with liquid to absorb a maximum amount of the $H_2S$ gas. The amount of liquid required to be circulated to obtain a given degree of $H_2S$ removal will depend on the chemical structure and basicity of the amino compound and on the partial pressure of $H_2S$ in the feed gas. Gas mixtures with low partial pressures such as those encountered in thermal conversion processes will require more liquid under the same absorption conditions than gases with higher partial pressures such as shale oil retort gases.

A typical procedure for the selective $H_2S$ removal phase of the process comprises selectively absorbing $H_2S$ via countercurrent contact of the gaseous mixture containing $H_2S$ and $CO_2$ with the solution of the amino compound in a column containing a plurality of trays at a low temperature, e.g., below 45° C., and at a gas velocity of at least about 0.3 ft/sec (based on "active" or aerated tray surface), depending on the operating pressure of gas, said tray column having fewer than 20 contacting trays, with, e.g., 4-16 trays being typically employed.

After contacting the normally gaseous mixture with the absorbent solution, which becomes saturated or partially saturated with $H_2S$, the solution may be at least partially regenerated so that it may be recycled back to the absorber. As with absorption, the regeneration may take place in a single liquid phase. Regeneration or desorption of the absorbent solution may be accomplished by conventional means such as pressure reduction of the solution or increase of temperature to a point at which the absorbed $H_2S$ flashes off, or bypassing the solution into a vessel of similar construction to that used in the absorption step, at the upper portion of the vessel, and passing an inert gas such as air or nitrogen or preferably steam upwardly through the vessel. The temperature of the solution during the regeneration step should be in the range from about 50° C. to about 170° C., and preferably from about 80° C. to 120° C., and the pressure of the solution on regeneration should range from about 0.5 to about 100 psia, preferably 1 to about 50 psia. The absorbent solution, after being cleansed of at least a portion of the $H_2S$ gas, may be recycled back to the absorbing vessel. Makeup absorbent may be added as needed.

In the preferred regeneration technique, the $H_2S$-rich solution is sent to the regenerator wherein the absorbed components are stripped by the steam which is generated by reboiling the solution. Pressure in the flash drum and stripper is usually 1 to about 50 psia, preferably 15 to about 30 psia, and the temperature is typically in the range from about 50° C. to 170° C., preferably about 80° C. to 120° C. Stripper and flash temperatures will, of course, depend on stripper pressure, thus at about 15 to 30 psia stripper pressures, the temperature will be about 80° C. to about 120° C. during desorption. Heating of the solution to be regenerated may very suitably be effected by means of indirect heating with low-pressure steam. It is also possible, however, to use direct injection of steam.

In one embodiment for practicing the entire process herein, as illustrated in FIG. 1, the gas mixture to be purified is introduced through line 1 into the lower portion of a gas-liquid countercurrent contacting column 2, said contacting column having a lower section 3 and an upper section 4. The upper and lower sections may be segregated by one or a plurality of packed beds as desired. The absorbent solution as described above is introduced into the upper portion of the column through a pipe 5. The solution flowing to the bottom of the column encounters the gas flowing countercurrently and dissolves the $H_2S$ preferentially. The gas freed from most of the $H_2S$ exits through a pipe 6, for final use. The solution, containing mainly $H_2S$ and some $CO_2$, flow toward the bottom portion of the column, from which it is discharged through pipe 7. The solution is then pumped via optional pump 8 through an optional heat exchanger and cooler 9 disposed in pipe 7, which allows the hot solution from the regenerator 12 to exchange heat with the cooler solution from the absorber column 2 for energy conservation. The solution is entered via pipe 7 to a flash drum 10 equipped with a line (not shown) which vents to line 13 and then introduced by pipe 11 into the upper portion of the regenerator 12, which is equipped with several plates and effects the desorption of the $H_2S$ and $CO_2$ gases carried along in the solution. This acid gas is passed through a pipe 13 into a condenser 14 wherein cooling and condensation of water and amine solution from the gas occur. The gas then enters a separator 15 where further condensation is effected. The condensed solution is returned through pipe 16 to the upper portion of the regenerator 12. The gas remaining from the condensation, which contains $H_2S$ and some $CO_2$, is removed through pipe 17 for final disposal (e.g., to a vent or incinerator or to an apparatus which converts the $H_2S$ to sulfur, such as a Claus unit or a Stretford conversion unit (not shown).

The solution is liberated from most of the gas which it contains while flowing downward through the regenerator 12 and exits through pipe 18 at the bottom of the regenerator for transfer to a reboiler 19. Reboiler 19, equipped with an external source of heat (e.g., steam injected through pipe 20 and the condensate exits through a second pipe (not shown)), vaporizes a portion of this solution (mainly water) to drive further $H_2S$ therefrom. The $H_2S$ and steam driven off are returned via pipe 21 to the lower section of the regenerator 12 and exited through pipe 13 for entry into the condensation stages of gas treatment. The solution remaining in the reboiler 19 is drawn through pipe 22, cooled in heat exchanger 9, and introduced via the action of pump 23 (optional if pressure is sufficiently high) through pipe 5 into the absorber column 2.

Typically, a gaseous stream to be treated having a 1:10 mole ratio of $H_2S:CO_2$ from an apparatus for thermal conversion of heavy residual oil, or a Lurgi coal gas having a mole ratio of $H_2S:CO_2$ of less than 1:10 will yield an acid gas having a mole ratio of $H_2S:CO_2$ of about 1:1 after treatment by the process of the present invention. The process herein may be used in conjunction with another $H_2S$ selective removal process; however, it is preferred to carry out the process of this invention by itself, since the amino compounds are extremely effective by themselves in preferential absorption of $H_2S$.

General Experimental Procedure

Procedure to Make Half-Salt of Tetradecahydro-Phenazine (TDP)

Into a 3 dram vial were added 0.204 g (1.291 mmol) benzene sulfonic acid, 1.2 grams toluene and 0.11 g methanol. A clear and colorless liquid resulted.

Into a second 3 dram vial were added 0.499 g (2.58 mmol) of tetradecahydro-phenazine (TDP), 4.18 g toluene and 0.14 g methanol. The mixture was heated to 35° C., a clear and colorless liquid results. A magnetic stirring bar was added to the TDP solution. With magnetic stirring at 35° C., the benzene sulfonic acid solution was added dropwise to the TDP solution. A clear and colorless liquid resulted at 35° C. and was allowed to cool to room temperature. At room temperature some crystallization occurred. The solution was chilled to 10° C. to obtain additional product. The clear and colorless liquid was decanted off the crystallized product. The solids remaining were washed with 2×3 ml of cold toluene. The excess toluene was removed under high vacuum at room temperature. 500 mg of white crystalline product was obtained.

1. Absorption tests were carried out at 35° C. on 0.15 M aqueous solutions of absorbent using a gas mixture of nitrogen:carbon dioxide:hydrogen sulfide of 89:10:1 for 2 hours.
2. Desorptions were run at 85° C. in flowing $N_2$ for 2 hours at the same flow rate as the test gas mixture.

| Compound | Molecular Weight | Selectivity | Loading (%) | Capacity (%) | Selectivity-Reabsorption |
|---|---|---|---|---|---|
| EETB (U.S. Pat. No. 4,405,585) | 161.24 | 15.4 | 16.3 | 60 | 13.3 |
| EETB (U.S. Pat. No. 4,405,585) | 161.24 | 12.6 | 19.1 | 58.1 | 11.2 |
| Bis-SE (U.S. Pat. No. 4,405,583) | 216.36 | 16.7 | 28.2 | 80 | 25.2 |
| TDP BSA half-salt[(1)] | 352.49 | 62.4 | 2.14 | 46.9 | 42.1 |
| DMTDP BSA half-salt[(2)] | 380.55 | 62.4 | 20.2 | 46.9 | 42.1 |

[(1)]half-salt tetradecahydro-phenazine (TDP) with benzene sulfonic acid
[(2)]half-salt of N,N-dimethyltetradecahydro-phenazine (DMTDP) with benzene sulfonic acid

The invention claimed is:

1. A process for the selective removal of one or more acidic components from normally gaseous mixtures containing such acidic components and $CO_2$ comprising contacting the normally gaseous mixture with an amino-containing absorbent comprising one or more material of the formula:

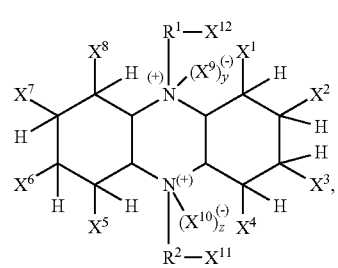

I

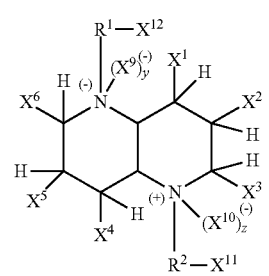

II and all isomers thereof

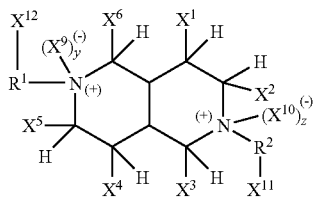

and all isomers thereof,

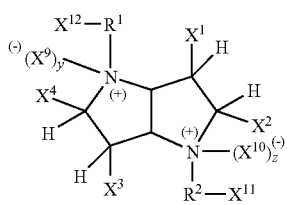

and isomers thereof,

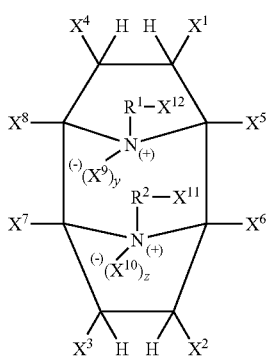

wherein $R^1$ and $R^2$ are the same or different and are selected from hydrogen methyl, ethyl, $C_3$-$C_9$ substituted or unsubstituted straight or branched alkyl, alkenyl, cycloalkyl, $C_6$-$C_9$ aryl, alkylaryl, arylalkyl;

$X^1$-$X^8$ are the same or different and are selected from hydrogen, methyl, ethyl, $C_3$-$C_9$ substituted or unsubstituted straight or branched alkyl, alkenyl, cycloalkyl, $C_6$-$C_9$ aryl, alkylaryl, arylalkyl, a functional group containing one or more oxygens, $X^9$ and $X^{10}$ are the same or different and are selected from —$(HO_3SR^4)^+$, —$(HO_3PR^4)^+$,

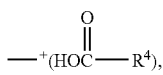

sulfonates, sulfates, sulfites, phosphates, phosphites, phosphonates, $C_1$-$C_9$ alkylates, adipates, benzoates, $X^{11}$ and $X^{12}$ are the same or different and are selected from hydrogen, a functional group containing one or more oxygens, wherein when $R^1$ and/or $R^2$ are $C_2$ or greater, the substituent $X^{11}$ or $X^{12}$, when other than H, is on the #2 carbon or higher, y is zero or 1, z is zero or 1, wherein, when $X^1$-$X^8$ and $X^{11}$ and $X^{12}$ are not functional groups containing at least one oxygen, at least one of Y and Z is 1, provided that when any of $X^1$-$X^8$, $X^{11}$ or $X^{12}$ is a functional group containing a single oxygen at least two of $X^1$ to $X^8$, $X^{11}$ or $X^{12}$ are such single oxygen containing functional groups and $R^4$ is selected from $C_1$-$C_9$ alkyl, $C_2$-$C_9$ alkenyl, $C_3$-$C_9$ cycloalkyl, $C_6$-$C_9$ aryl, alkylaryl or arylalkyl, under conditions suitable for the selective removal of one or more of the gaseous acidic components from said mixture.

2. The process of claim 1 wherein the absorbent comprises one or more materials of the formula:

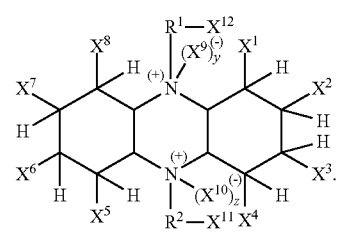

3. The process of claim 1 wherein the absorbent comprises one or more materials of the formula

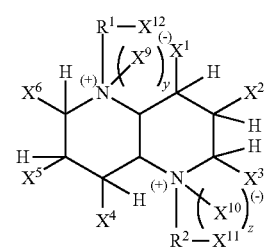

and all isomers thereof.

4. The process of claim 1 wherein the absorbent comprises one or more materials of the formula:

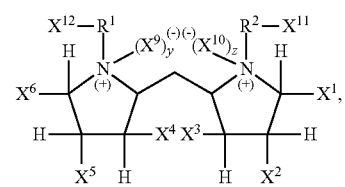

and all isomers thereof.

5. The process of claim 1 wherein the absorbent comprises one or more materials of the formula:

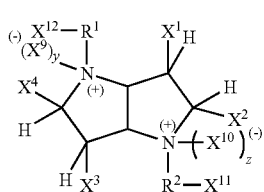

and all isomers thereof.

6. The process of claim 1 wherein the absorbent comprises one or more materials of the formula:

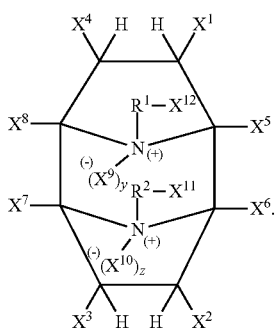

7. The process of claim 1, 2, 3, 4, 5 or 6 wherein when one or more of $X^1$-$X^8$, $X^{11}$ and $X^{12}$ are functional groups containing at least one oxygen, Y and Z are both zero.

8. The process of claim 1, 2, 3, 4, 5 or 6 wherein $X^1$-$X^8$ are selected from the group consisting of:

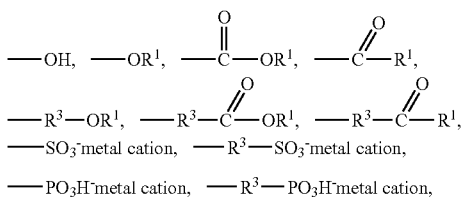

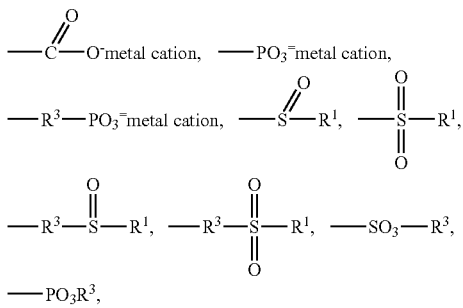

and mixtures thereof, wherein $R^3$ is selected from $C_1$-$C_9$ alkyl, $C_2$-$C_9$ alkenyl, $C_3$-$C_9$ cycloalkyl, $C_6$-$C_9$ aryl, alkylaryl or arylalkyl, and metal cation is one or more monovalent, divalent or trivalent metal cation sufficient to satisfy the valence requirement of the anion or anion cluster.

9. An absorbent for the selective removal of acidic components from normally gaseous mixture containing such acidic components and non-acidic components and $CO_2$, said absorbent being of the formula:

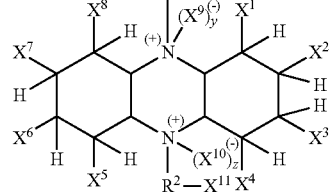

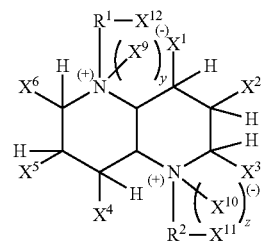

and all isomers thereof,

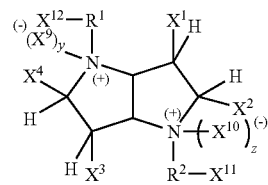

and all isomers thereof,

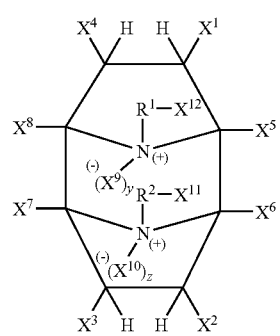

wherein $R^1$ and $R^2$ are the same or different and are selected from hydrogen methyl, ethyl, $C_3$-$C_9$ substituted or unsubstituted straight or branched alkyl, alkenyl, cycloalkyl, $C_6$-$C_9$ aryl, alkylaryl, arylalkyl;

$X^1$-$X^8$ are the same or different and are selected from hydrogen, methyl, ethyl, $C_3$-$C_9$ substituted or unsubstituted straight or branched alkyl, alkenyl, cycloalkyl, $C_6$-$C_9$ aryl, alkyl aryl, arylalkyl, a functional group containing one or more oxygens, $X^9$ and $X^{10}$ are the same or different and are selected from $—(HO_3SR^4)^+$, $—(HO_3PR^4)^+$,

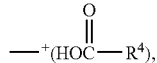

sulfonates, sulfates, sulfites, phosphates, phosphites, phosphonates, $C_1$-$C_9$ alkylates, adipates, benzoates, $X^{11}$ and $X^{12}$ are the same or different and are selected from hydrogen, a functional group containing one or more oxygens, wherein when $R^1$ and/or $R^2$ are $C_2$ or greater, the substituent $X^{11}$ or $X^{12}$, when other than H, is on the #2 carbon or higher, y is zero or 1, z is zero or 1, wherein, when $X^1$-$X^8$ and $X^{11}$ and $X^{12}$ are not functional groups containing at least one oxygen, at least one of Y and Z is 1, provided that when any of $X^1$-$X^8$, $X^{11}$ or $X^{12}$ is a functional group containing a single oxygen at least two of $X^1$ to $X^8$, $X^{11}$ or $X^{12}$ are such single oxygen containing functional group and $R^4$ is selected from $C_1$-$C_9$ alkyl, $C_2$-$C_9$ alkenyl, $C_3$-$C_9$ cycloalkyl, $C_6$-$C_9$ aryl, alkylaryl or arylalkyl, under conditions suitable for the selective removal of one or more of the gaseous acidic components from said mixture.

10. The absorbent of claim 9 of the formula:

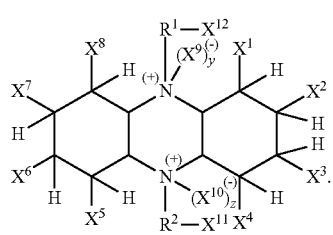

I

11. The absorbent of claim 9 of the formula:

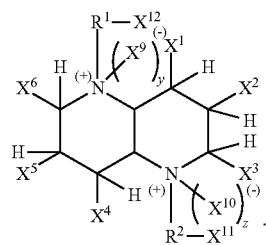

12. The absorbent of claim 9 of the formula:

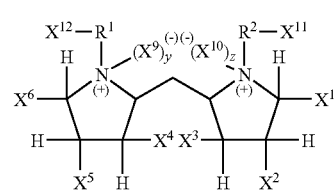

III and all isomers thereof.

13. The absorbent of claim 9 of the formula:

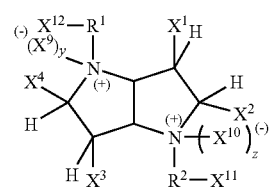

IV and all isomers thereof.

14. The absorbent of claim 9 of the formula:

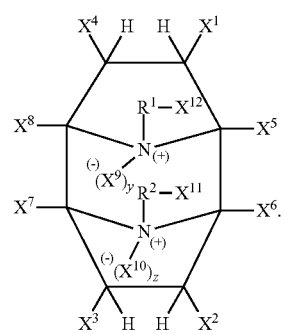

V

15. The absorbent of claim 9, 10, 11, 12, 13 or 14 wherein when one or more of $X^1$-$X^8$, $X^{11}$ and $X^{12}$ are functional groups containing at least one oxygen, Y and Z are both zero.

16. The absorbent of claim 9, 10, 11, 12, 13 or 14 wherein $X^1$-$X^8$ are selected from the group consisting of:

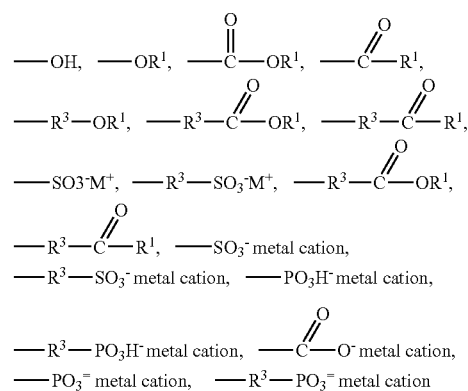

-continued
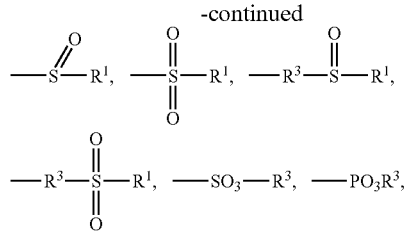
and mixtures thereof,
wherein $R^3$ is selected from $C_1$-$C_9$ alkyl, $C_2$-$C_9$ alkenyl, $C_3$-$C_9$ cycloalkyl, $C_6$-$C_9$ aryl, alkylaryl or aryl alkyl, and metal cation is one or more monovalent, divalent or trivalent metal cation to satisfy the valence requirement of the anion or anion cluster.
* * * * *